(12) United States Patent
Choi et al.

(10) Patent No.: US 11,650,622 B2
(45) Date of Patent: May 16, 2023

(54) LIGHTING DEVICE FOR ACQUIRING NOSE PATTERN IMAGE

(71) Applicant: ISCILAB CORPORATION, Seoul (KR)

(72) Inventors: Hyeong In Choi, Seoul (KR); Stephanie Sujin Choi, Seoul (KR)

(73) Assignee: ISCILAB CORPORATION, Seoul (KR)

( * ) Notice: Subject to any disclaimer, the term of this patent is extended or adjusted under 35 U.S.C. 154(b) by 272 days.

(21) Appl. No.: 17/271,327

(22) PCT Filed: Aug. 23, 2019

(86) PCT No.: PCT/KR2019/010740
§ 371 (c)(1),
(2) Date: Jul. 12, 2021

(87) PCT Pub. No.: WO2020/045899
PCT Pub. Date: Mar. 5, 2020

(65) Prior Publication Data
US 2021/0342581 A1    Nov. 4, 2021

(30) Foreign Application Priority Data

Aug. 29, 2018  (KR) .......................... 10-2018-0101804

(51) Int. Cl.
*G06F 1/16* (2006.01)
*G06V 40/10* (2022.01)
*A61B 1/06* (2006.01)
*H04N 23/74* (2023.01)
*G06V 10/10* (2022.01)

(52) U.S. Cl.
CPC .............. *G06F 1/1607* (2013.01); *A61B 1/06* (2013.01); *G06F 1/1605* (2013.01); *G06F 1/1686* (2013.01); *G06V 10/10* (2022.01); *G06V 40/10* (2022.01); *H04N 23/74* (2023.01)

(58) Field of Classification Search
CPC . F21V 33/00; A61B 1/233; A61B 1/06; G06F 1/1686; G06F 1/1626; G06F 1/1605; G06F 1/1607; H04N 23/56; H04N 23/74; G03B 15/05; G03B 30/00; G03B 2215/0567; H04M 1/725; H04M 1/21; G06V 10/10; G06V 40/10
See application file for complete search history.

(56) References Cited

U.S. PATENT DOCUMENTS

| 9,443,166 | B2 * | 9/2016 | Kinard | .................... A01K 11/00 |
| 10,552,673 | B2 * | 2/2020 | Wee | ........................ A01K 15/04 |
| 10,565,440 | B2 * | 2/2020 | Wee | ........................ A61B 5/6819 |

(Continued)

FOREIGN PATENT DOCUMENTS

| EP | 3029603 | A2 * | 6/2016 | ........... A01K 11/006 |
| JP | 6840703 | B2 * | 3/2021 | ........... A01K 11/006 |

(Continued)

*Primary Examiner* — Vinh T Lam
(74) *Attorney, Agent, or Firm* — LRK Patent Law Firm

(57) ABSTRACT

The present invention is a lighting device attached to the front of a camera device, such as a smartphone, and connected to the camera device to produce an appropriate lighting environment for the acquisition of good quality animal nose pattern images by taking into consideration such factors and ambient lighting as well as the color of the nose.

13 Claims, 7 Drawing Sheets

(56) References Cited

U.S. PATENT DOCUMENTS

| | | | | |
|---|---|---|---|---|
| 11,019,250 B2 * | 5/2021 | Choi | ................... | H04N 23/633 |
| 11,025,803 B2 * | 6/2021 | Choi | ...................... | H04N 23/55 |
| 2012/0320340 A1 * | 12/2012 | Coleman, III | ........... | A61B 3/10 |
| | | | | 351/208 |
| 2016/0259970 A1 * | 9/2016 | Wee | ..................... | G06T 7/0012 |

FOREIGN PATENT DOCUMENTS

| | | | | |
|---|---|---|---|---|
| KR | 10-2013-0080574 A | 7/2013 | | |
| KR | 10-2015-0018973 A | 2/2015 | | |
| KR | 10-1494716 B1 | 2/2015 | | |
| KR | 10-1494717 B1 | 2/2015 | | |
| KR | 10-1527801 B1 | 6/2015 | | |
| KR | 10-1757441 B1 | 7/2017 | | |
| KR | 10-2017-0138139 A | 12/2017 | | |
| KR | 10-2018-0088540 A | 8/2018 | | |
| WO | WO-2014189250 A2 * | 11/2014 | ........... | A01K 11/006 |
| WO | WO-2015041833 A1 * | 3/2015 | ......... | G06K 9/00597 |
| WO | WO-2019074496 A1 * | 4/2019 | ........... | A01K 11/006 |
| WO | WO-2020036368 A1 * | 2/2020 | ........... | A01K 11/006 |

* cited by examiner

LIGHTING DEVICE FOR ACQUIRING NOSE PATTERN IMAGE

CROSS-REFERENCE TO RELATED APPLICATIONS

The present application is a U.S. National Phase entry from International Application No. PCT/KR2019/010740, filed Aug. 23, 2019, which claims priority to Korean Patent Application No. 10-2018-0101804, filed Aug. 29, 2018 the disclosure of which is incorporated by reference herein in their entirety.

TECHNICAL FIELD

The present invention is a lighting device attached to the front of a camera device, such as a smartphone, and connected to the camera device to produce an appropriate lighting environment for the acquisition of good quality animal nose pattern images by taking into consideration such factors and ambient lighting as well as the color of the nose.

BACKGROUND ART

The practice of nose pattern printing (muzzle printing) using ink impression printing for comparing identity for mainly cows and sheep began in the latter half of the $20^{th}$ century. However, many traditional methods used primitive means and presented many difficulties.

For example, with the exception of methods using paint to obtain impressions, most other identification methods involve damage to a specific part of the animal in the process, which may cause pain and rejection in the animal and thereby endanger both the operator and the animal, and also may require a lot of work time.

In contact nose printing methods a pigment is applied to the nose surface for a contact impression print or a capacitive touch sensor, such as those used for fingerprinting, is used to acquire nose pattern images.

The ink impression method has long been used to identify cows in Japan. However, the contact method has a high risk of creating a distorted impression due to excessive ink application on the nose that causes the ink to seep into the grooves of the nose, resulting in the loss of detail, as well as applying uneven pressure.

The prior art is as follows:
(Patent Document 1) Korean Patent Registration No. 10-1527801
(Patent Document 2) Korean Patent Registration No. 10-1494717
(Patent Document 3) Korean Patent Registration No. 10-1494716

DISCLOSURE

Technical Problem

The problem to be solved by the present invention is the prevention or minimization of obstructive reflections from the moisture on the surface of an animal's nose when using a camera device, such as a smartphone, to acquire good quality nose pattern images that can be used for animal identify registration or verification, by providing a lighting device that produces indirect illumination rather than direct lighting.

The present invention also pertains to the lighting device having an indirect illumination unit and a suction unit, wherein the suction unit is configured to affix the indirect illumination unit in front of the camera lens used for nose pattern image acquisition.

The lighting device in the present invention also connects electrically to the camera device, such as a smartphone, for power supply, and to be operated by the control program installed in the camera device.

The lighting device also comprises a light source, such as an LED, as well as a circuit board that includes a power supply circuit and microprocessor for power control signals positioned at the base of the indirect illumination unit.

The present invention also provides a lighting device wherein the indirect illumination unit and the suction unit are integrally formed as a single unit, or manufactured as separate units.

Technical Solution

The present invention is a lighting device for acquiring good quality nose pattern images on camera devices, such as smartphones, comprising an indirect illumination unit that can be easily attached in front of the camera lens using a suction unit that is integrally formed as a single unit with the indirect illumination unit, or manufactured separately and fastened together.

The indirect illumination unit of the present lighting device also comprises a light source (LED, or other small light emitters) positioned at the base as well as an indirect illumination casing for producing indirect lighting onto the nose surface.

The indirect illumination casing is positioned on top of the light source at the base to cover the emitted light to produce indirect illumination. The indirect illumination casing is configured as two layers, the inner casing and the outer casing, that are separated by a distance at the bottom with the light being emitted between the two layers to produce indirect illumination within; and wherein the ideal embodiment has the inner casing and the outer casing converging at the top.

The light source at the base of the indirect illumination unit is powered through a connection to the camera device, such as a smartphone, and configured to interwork with the camera in the camera device.

Advantageous Effects

The present invention has the effect of prevention or minimization of obstructive reflections from the moisture on the surface of an animal's nose when using a camera device, such as a smartphone, to acquire good quality nose pattern images that can be used for animal identify registration or verification, by providing a lighting device that produces indirect illumination rather than direct lighting.

In the present invention, the indirect illumination unit is fastened onto the suction unit for easy attachment in front of the camera lens of a camera device, such as a smartphone, for the acquisition of nose pattern images.

The lighting device is connected electrically to the camera device, such as a smartphone, for power supply and receiving control signals from the control program installed in the camera device, thereby obviating the need for a separate controller device.

The lighting device also comprises a light source, such as an LED, as well as a circuit board that includes a power supply circuit and microprocessor for power control signals positioned at the base of the indirect illumination unit. The LED is installed on the circuit board and jointly controlled by the control program installed on the camera device and microprocessor on the circuit board, resulting in efficient illumination.

The indirect illumination unit and the suction unit in the present invention may be manufactured as a single unit or separately, thereby having the advantageous effect of being able to meet the various needs of consumers.

DETAILED DESCRIPTION OF THE INVENTION

Figure 1:
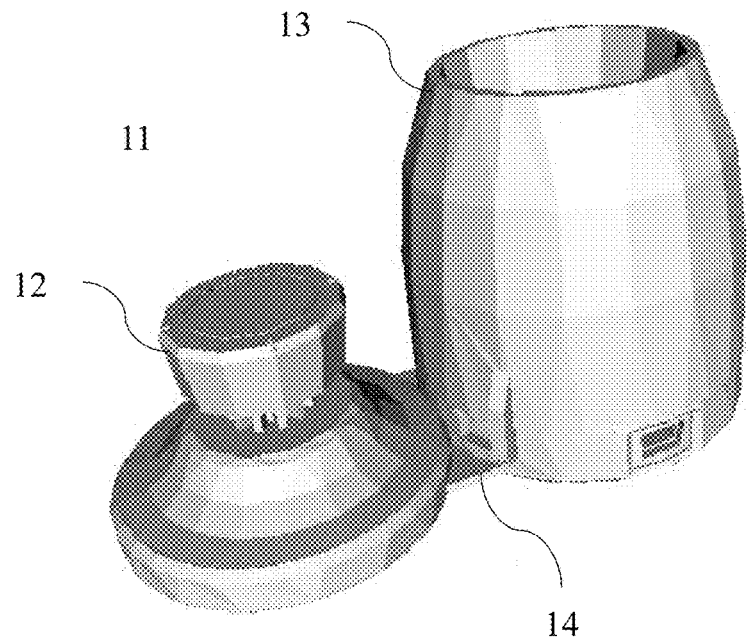
FIG. 1 illustrates an indirect illumination unit and a suction unit fastened together, or formed integrally together as a single unit.

The present invention is a lighting device 11 to be attached to the front of a camera device, such as a smartphone, using a vacuum suction unit 12, 21. The lighting device is connected to the camera device to produce an appropriate lighting environment for the acquisition of good quality animal nose pattern images that can be used for the biometric registration and verification of an animal's identity, by taking into consideration such factors and ambient lighting as well as the color of the nose.

The lighting device and the suction unit may be integrally molded, or manufactured separately and paired together. If manufactured separately, the lighting device may also comprise a pairing subunit 14, with the lighting device on one side and the suction unit to the other side. The fastening mechanism of the pairing subunit may comprise many means, including the use of bolts and nuts or a configuration in which the two joining components are inserted and locked into complementary grooves on either side.

The suction unit may be any conventional vacuum suction cup style mounting device or a similar or identical structure specially designed for the lighting device, so long as it can firmly affix the indirect illumination device that is fastened onto the suction unit to the front of the camera lens 24 by vacuum force.

The present invention also comprises an indirect illumination unit 13, which comprises a light source (such as LED lights, etc.) at the bottom of the lighting device, and indirect illumination casings 31 that produce indirect illumination onto the nose surface by diffusing the light from the light source. The casings may comprise an inner casing and an outer casing. While the inner casing and outer casing should be described as inner indirect illumination casing and outer indirect illumination casing, they are abbreviated as 'inner casing' and 'outer casing' for the sake of brevity.

FIG. 1 is a schematic diagram illustrating the lighting device when the indirect illumination unit and suction unit are integrally formed as a single unit, or made of two separate units fastened together by the fastener on a pairing subunit.

For clarification, in the present invention pairing subunit and fastener refer to mechanisms that join or fasten together two separate components, such as the indirect illumination unit and suction unit or a light source circuit board casing to the indirect illumination casings. These terms should be easily understood in context by those skilled in the art.

Figure 2:
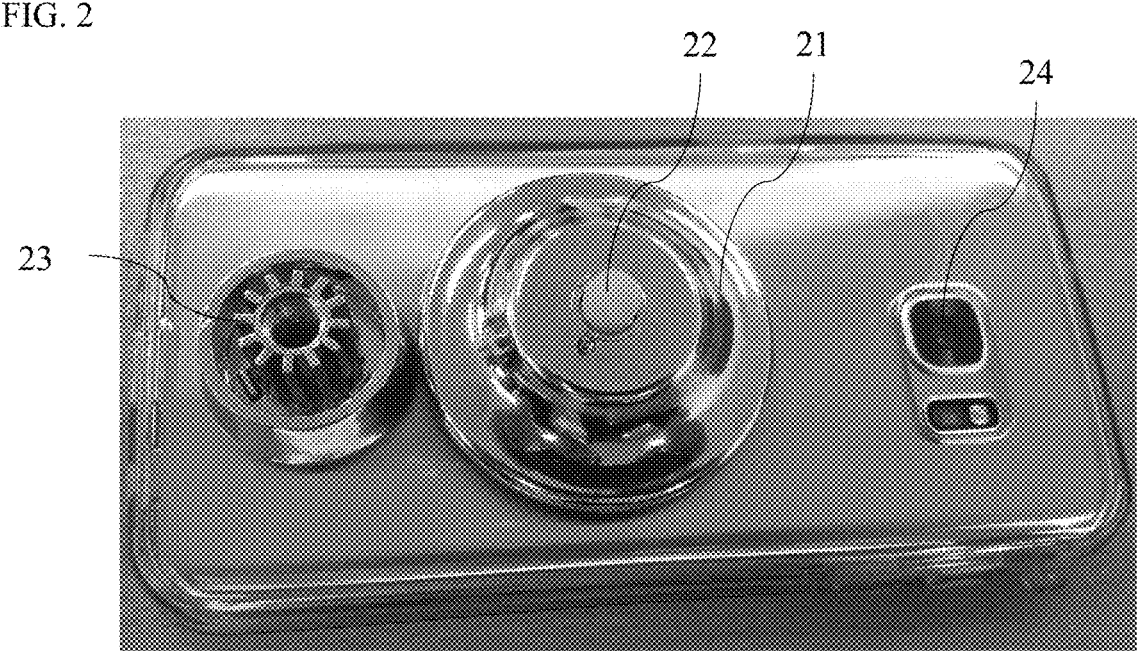
FIG. 2 shows an embodiment of a vacuum suction unit according to the present invention.

FIG. 2 illustrates one embodiment of the suction unit, wherein the nut 23 is tightened on the bolt 22 to create vacuum suction between the suction unit and smartphone device for firm attachment.

One possible method of attaching the indirect illumination unit in front of the camera lens is to have a pairing subunit, which extends to the side of the indirect illumination unit, with an opening through which the bolt of the suction unit goes, so that the side extension arm is fixed between the nut and bolt.

Figure 3:
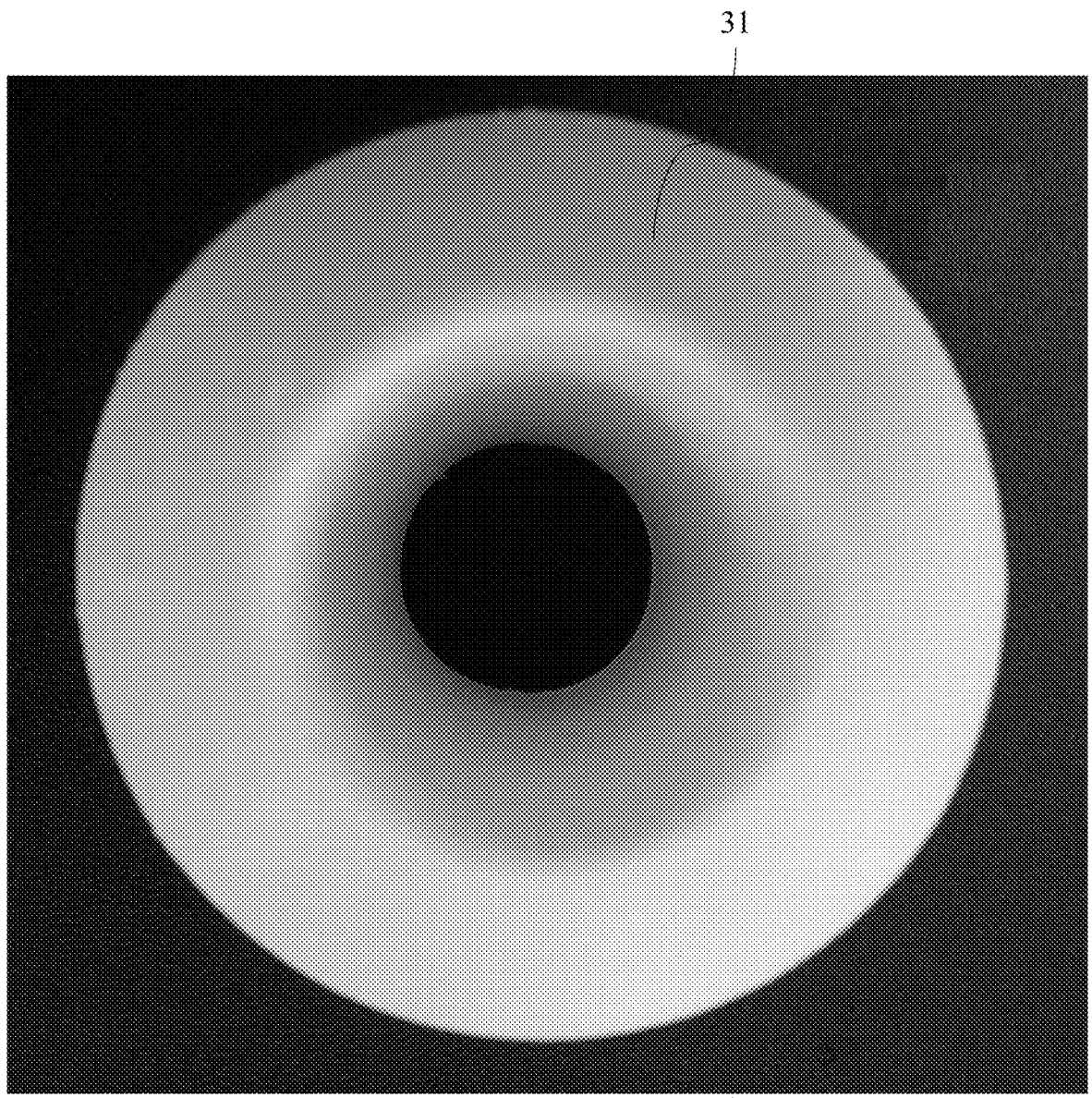
FIG. 3 shows an embodiment of an indirect illumination unit according to the present invention.
Figure 4:
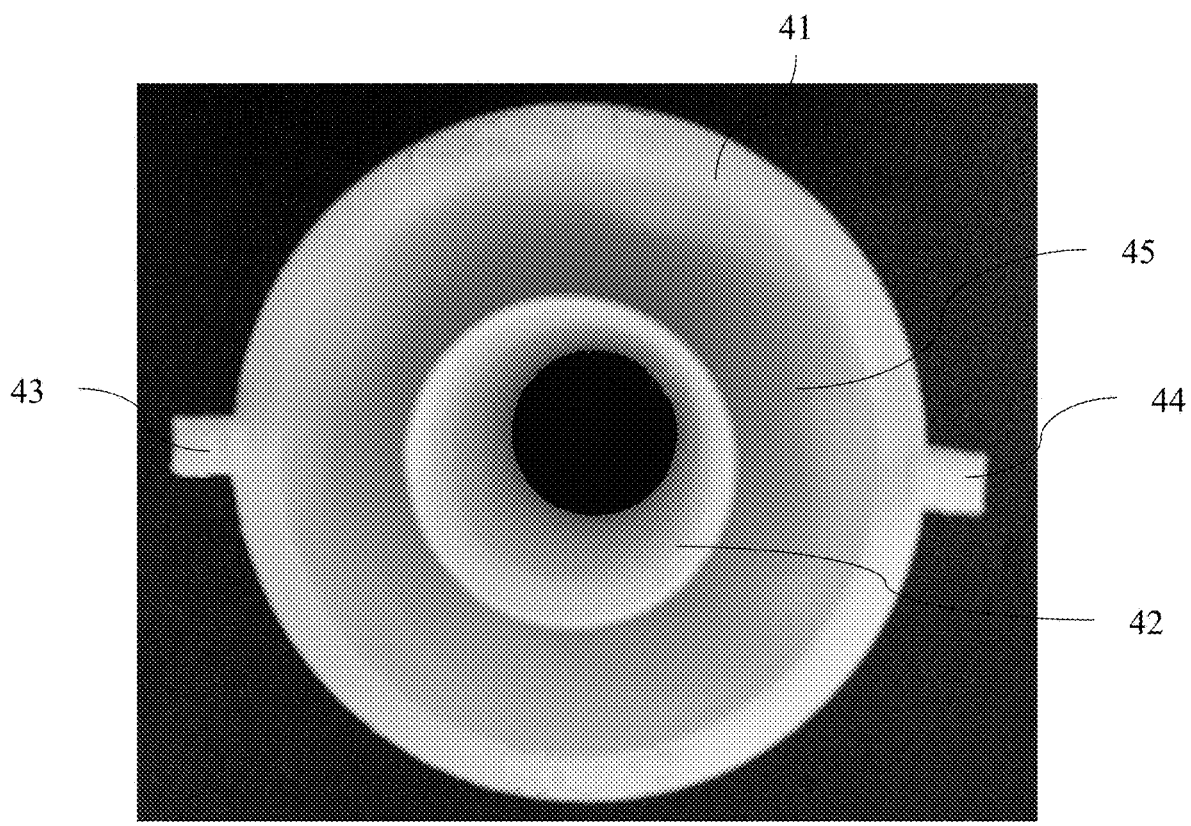
FIG. 4 is a bottom view of an inner casing and an outer casing of the indirect illumination unit of FIG. 3.

FIG. 3 shows an embodiment of the indirect illumination unit, and FIG. 4 shows the bottom side of the inner casing 42 and outer casing 41 of the indirect illumination unit of FIG. 3.

The outer casing in FIG. 4 shows a protruding fastener 43, 44 for complementary forced fitting. The means of fastening may be such a complementary forced fitting, or a conventional method like using nuts and bolts.

Figure 5:
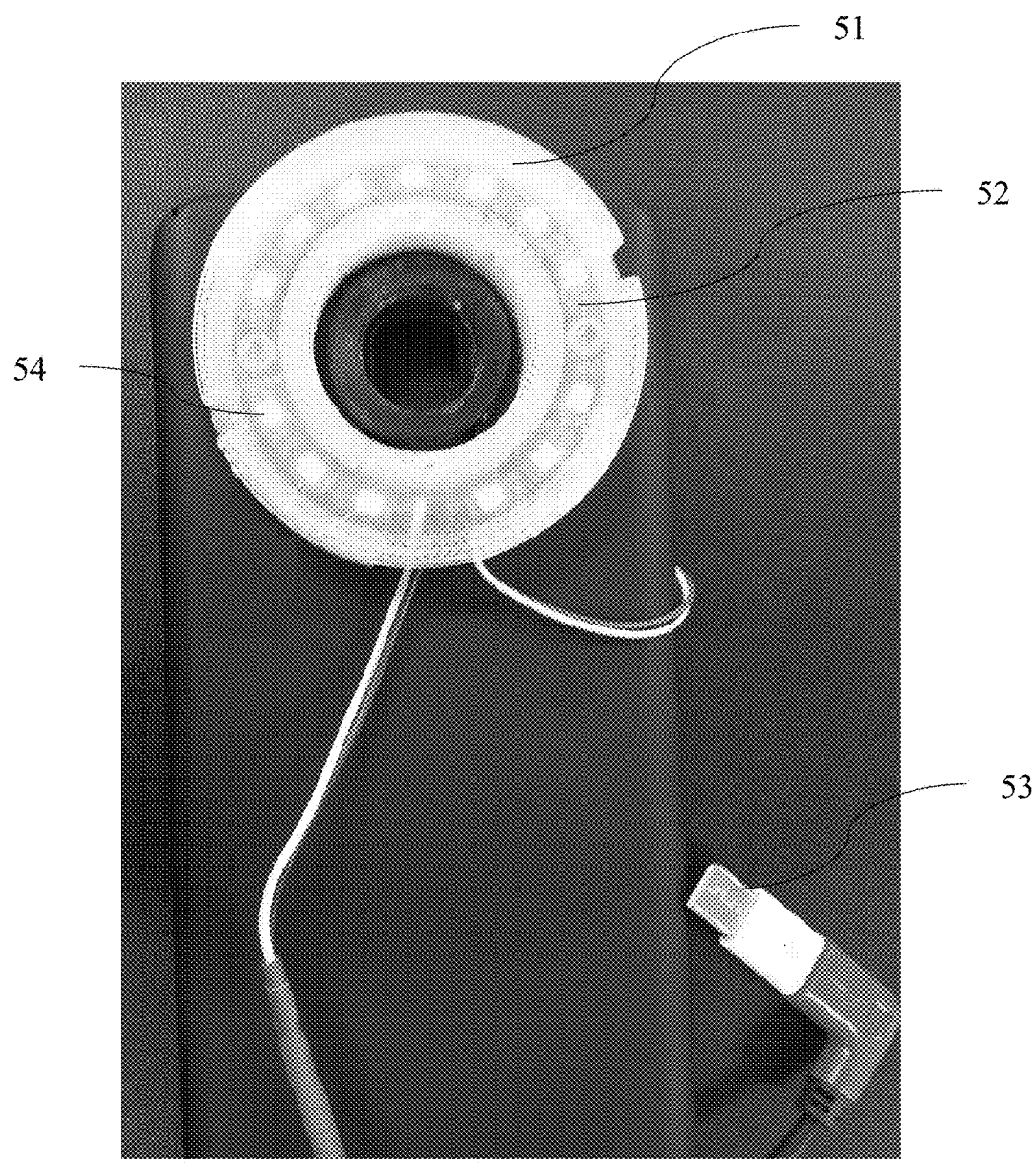
FIG. 5 shows a connection unit for connecting the light source circuit board to a smartphone for power and control signals.

FIG. 5 shows an example of a circuit board casing and a connection unit that relays power and control signals from the smartphone device.

The indirect illumination unit in the present invention is positioned at the top of the lighting device, and comprises an indirect illumination casing that covers the light from the light source 54 positioned at the bottom of the lighting device to produce indirect illumination. The indirect illumination casing comprises two layers, an inner casing and an outer casing, that separate at a certain distance at the bottom and converge at the top, thereby forming a single unit. The light from the light source is emitted into the diffusion space 45 between the inner casing and the outer casing, and diffused through the inner casing to indirectly illuminate the nose surface.

The inner casing and outer casing may be configured to be separate components that are joined together for use. The inner casing may have varying inner diameters at the top, bottom, and middle.

An ideal embodiment of the indirect illumination unit is 40 mm to 90 mm in length from top to bottom, but the length may deviate from the ideal range depending on such factors as the focal length of the camera or the size of the light source or circuit board. The shape of the inner casing is preferably a cylindrical dome to produce uniformly diffused light inside, but it may polygonal or oval depending on consumer needs or aesthetics. Taking into consideration the size of an animal's nose, the inner diameter of the inner casing is preferably between 10 mm and 50 mm, but the diameter may deviate from this range depending on such factors as the size of the nose or the focal length of the camera.

The indirect illumination casing and the circuit board casing 51, which houses the light source-embedded circuit board 52, may be configured as separate components or as a single unit. When the indirect illumination casing and the circuit board casing are configured separately, a fastening mechanism may be used to join the two together, such as using nuts and bolts, or carving out complementary grooves and protrusions for forced fitting.

The indirect illumination is preferably made of white-tone color material, similar to that of a typical fluorescent lamp cover, but may be made of any other color. The outer casing and the inner casing may be made of different colors. The inner casing and outer casing of the indirect illumination unit may be different colors, and the outer casing may be made of transparent material or removed altogether to allow ambient light through completely.

FIG. 4 shows a space within which the light is reflected or diffused.

If the light source is not embedded on the circuit board but instead used on its own, the circuit board casing may be referred to as a light source casing. Such modifications can be made easily by a person skilled in the art by a simple design change.

The light source is positioned at the base of the lighting device, and may comprise one or more emitters. When there are two or more emitters, the emitters should be spaced evenly. Small LEDs are preferable as the light source but any type of light source, including a small lamp, which can be used for indirect illumination according to the present invention is sufficient.

In a preferred embodiment, the circuit board at the bottom on the indirect illumination unit comprises an embedded light source, a power supply circuit to power the light source, a microprocessor to control the luminance and illumination time of the light source, and a memory unit equipped with a control program. Power supply and control signals from the control program in the smartphone may be received from the smartphone through a connection unit 53. One side of the circuit board on which the light source and other electronic elements are mounted may also have a connection unit that connects the smartphone charging port to the power supply circuit and control signal line.

In one embodiment of the present invention, a smartphone app controls the connected lighting device, attached using the suction unit, during nose pattern image acquisition for the capture of good quality images.

In another embodiment, the control signals from a smartphone app and the microprocessor embedded in the lighting device interwork to control lighting luminance for the capture of good quality nose pattern images. An app that interworks with the lighting device and the smartphone camera may be provided through a separate memory unit or a separate app server.

In another embodiment, the memory in which the microprocessor and the control program are mounted may be omitted.

In the present invention, the light source at the base of the indirect illumination unit is configured to operate by power provided by a camera device, such as a smartphone, and in conjunction with the camera on the camera device.

According to the present invention, the acquisition of good quality nose pattern images comprises pressing the capture button to produce controlled lighting during which one or more nose pattern images are captured. When two or more nose pattern images have been captured, the best quality image may be selected to be used for registration and/or verification. In one instant, or within one second, about 10 to 20 nose pattern images may be acquired. The selection of the best quality image out of a plurality of captured images is made possible by installing on the smartphone the app provided by the present invention that contains an algorithm for such a purpose.

FIG. 5 shows an embodiment of a circuit board casing, which houses the circuit board on which the light source is embedded, that is positioned at the base of the lighting device.

As mentioned previously, the indirect illumination unit and the circuit board casing may be configured as separate components or as a single unit, and this configuration may be variously modified.

Any lighting device with a light source at the bottom, with the light from the light source transmitted through the inner casing and the outer casing to produce indirect illumination falls under the scope of the present invention.

Figure 6:
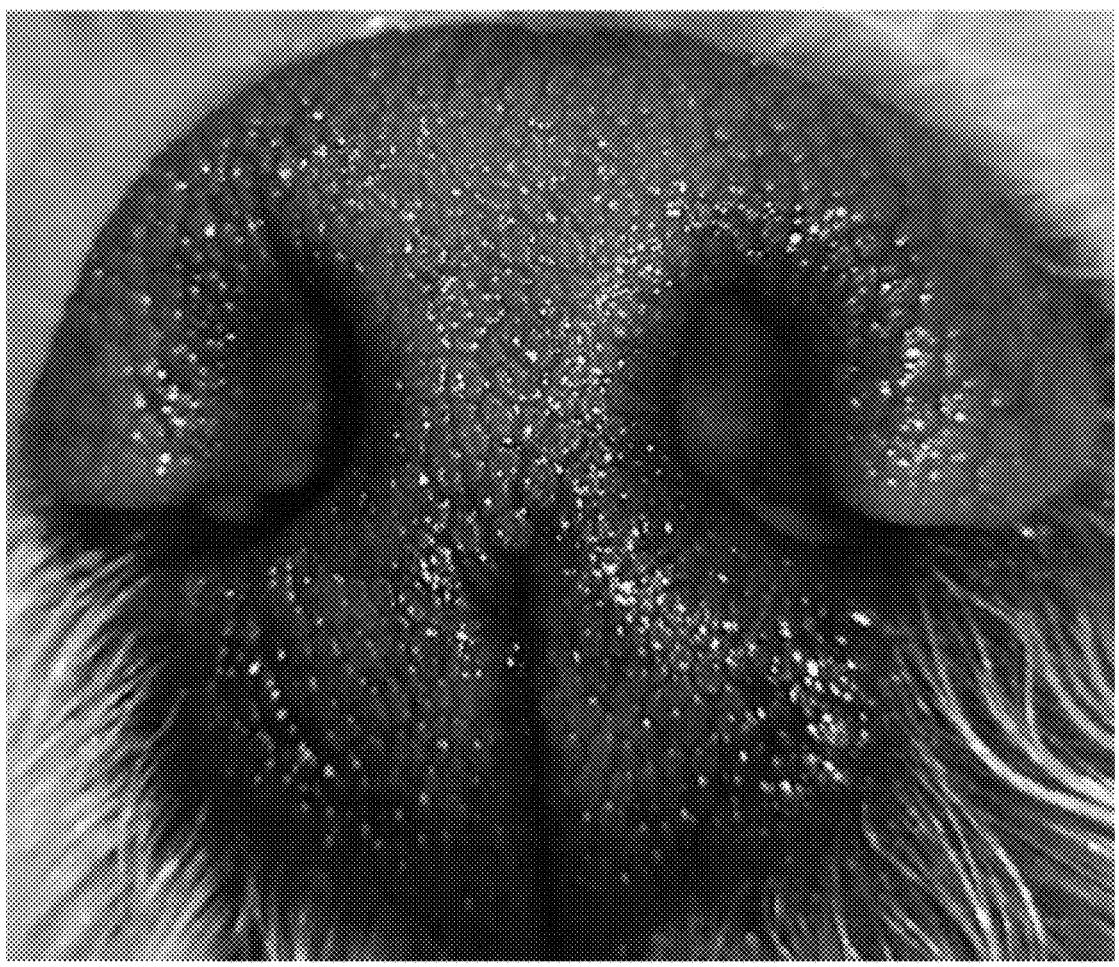
FIG. 6 is an example of a nose pattern image acquired using direct lighting.
Figure 7:
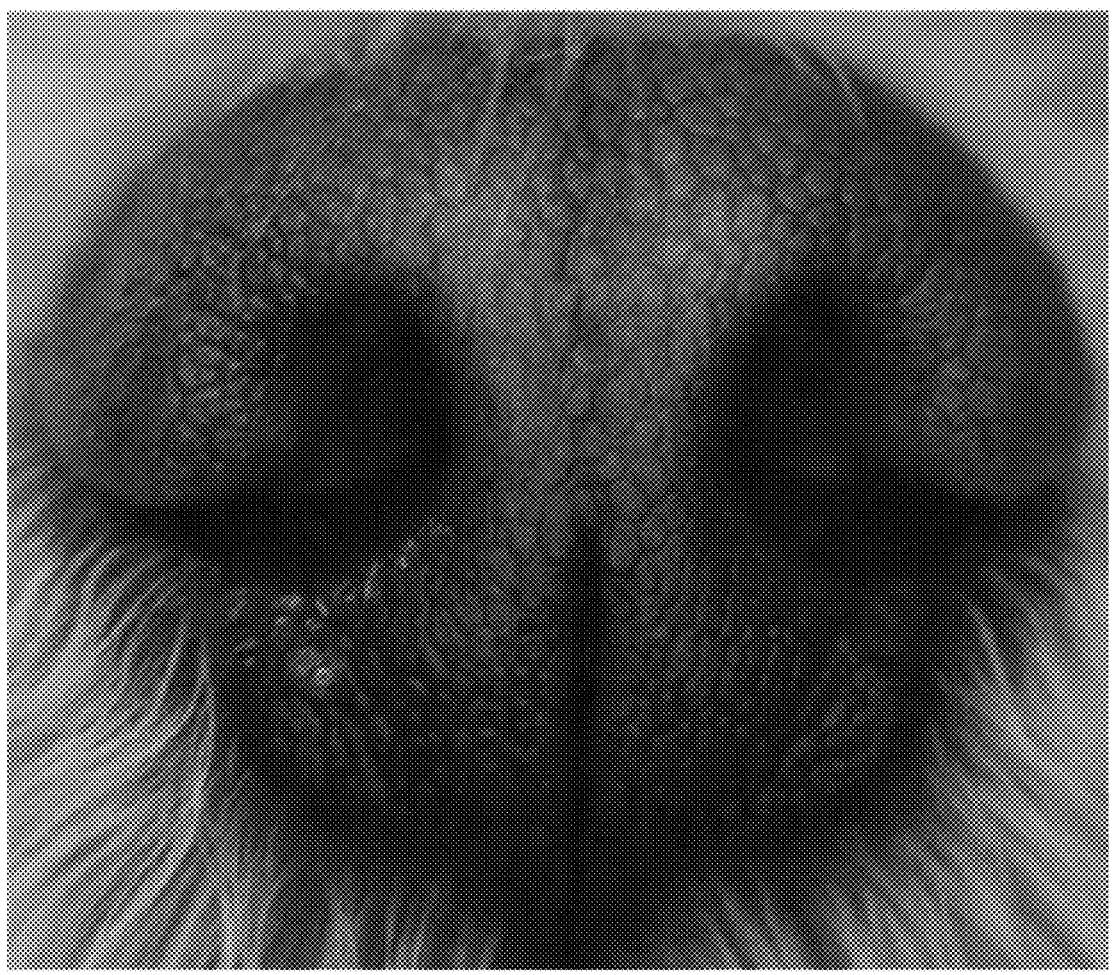
FIG. 7 is an example of a nose pattern image acquired using indirect illumination.

FIG. 6 is a nose pattern image captured using direct illumination, and FIG. 7 is a nose pattern image capture using indirect illumination. The nose pattern image in FIG. 7 is an example of a good quality image that is usable for biometric registration and verification.

Figure 8:
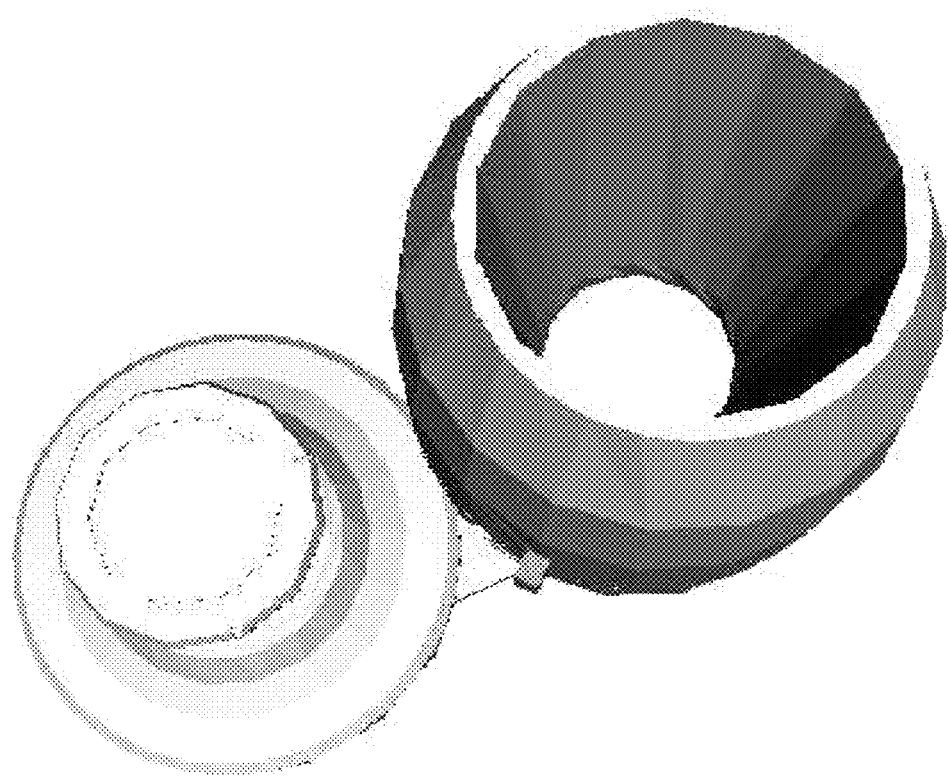
FIG. 8 is a top perspective view of a lighting device according to the present invention.
Figure 9:
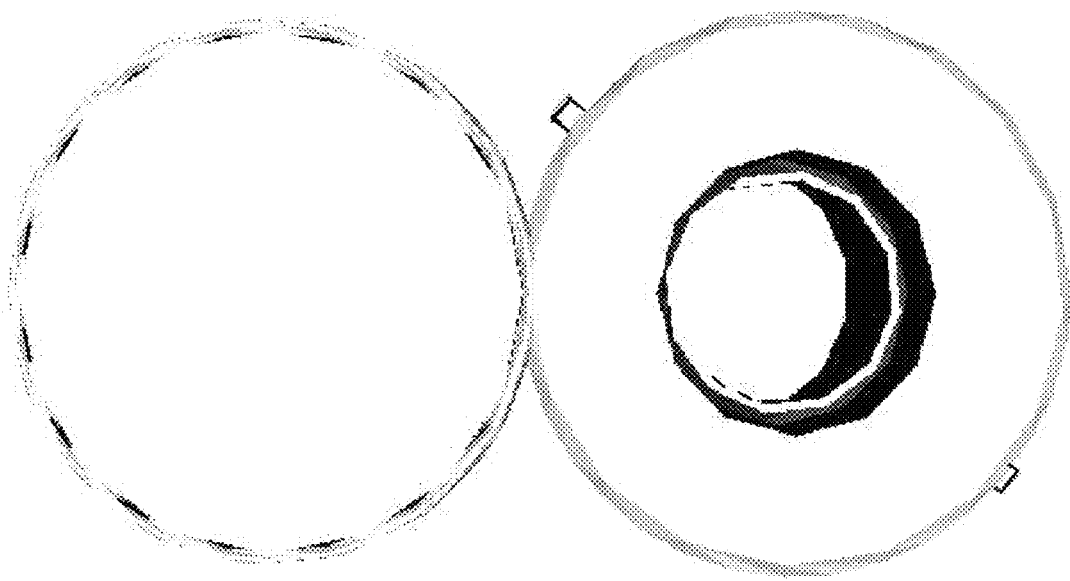
FIG. 9 is a bottom view of a lighting device according to the present invention.

FIG. 8 shows a top view of an embodiment of the lighting device, and FIG. 9 shows a bottom view.

INDUSTRIAL APPLICABILITY

The present invention is a lighting device attached to the front of a camera device, such as a smartphone, and connected to the camera device to produce an appropriate lighting environment for the acquisition of good quality animal nose pattern images by taking into consideration such factors and ambient lighting as well as the color of the nose, and therefore has high industrial applicability.

Reference numerals in the drawings are as follows:

| | | | |
|---|---|---|---|
| 11: | lighting device | | |
| 12: | vacuum suction unit | 13: | indirect illumination unit |
| 14: | pairing subunit | 21: | vacuum suction unit |
| 22: | bolt | 23: | nut |
| 31: | indirect illumination casing | | |
| 41: | outer casing | 42: | inner casing |
| 43, 44: | fastening means | 45: | space within which light is reflected |
| 51: | circuit board casing | | |
| 52: | circuit board on which light source is embedded | | |
| 53: | connection unit for power supply and control signals | | |
| 54: | lighting device | | |

What is claimed is:

1. A lighting device for acquiring nose pattern images, comprising:
    an indirect illumination unit attached to a front of a camera lens in a camera device, including a smartphone;
    a pairing subunit onto which the indirect illumination unit is fastened; and
    a suction unit that affixes the indirect illumination unit in front of the camera lens.

2. The lighting device of claim 1, wherein the indirect illumination unit comprises a light source at a bottom, and an inner casing and an outer casing to produce indirect illumination with a light from the light source.

3. The lighting device of claim 2, wherein:
    the light source is positioned at the bottom of the indirect illumination unit in a space between the inner casing and the outer casing, and
    the inner casing and the outer casing are convergent at a top to form a single unit.

4. The lighting device of claim 3, wherein:
the inner casing and the outer casing diffuse the light from the light source through the inner casing to produce indirect illumination, and
the inner casing and the outer casing are made with a white-tone color to allow ambient light to enter through to the inside of the indirect illumination unit.

5. The lighting device of claim 1, wherein an outer casing is made of transparent material or removed altogether to allow ambient light through completely.

6. The lighting device of claim 1, wherein the indirect illumination unit and the suction unit are made as a single unit, or are made of two separate units and joined together.

7. The lighting device of claim 1, wherein the light source and a circuit board with a power supply circuit and a control signal line are affixed at a bottom of the indirect illumination unit between the inner casing and the outer casing.

8. The lighting device of claim 7, wherein the circuit board comprises a microprocessor for controlling luminance and illumination time by connecting to the smartphone and a memory unit equipped with a control program.

9. The lighting device of claim 7, wherein the circuit board is connected to the smartphone through a connection unit for power supply and control signals.

10. The lighting device of claim 8, wherein a connection unit relays control signals from the control program in the smartphone for the acquisition of good quality nose pattern images.

11. The lighting device of claim 3, wherein an upper and a lower diameters of the inner casing and the outer casing vary according to at least one out of the factors consisting of
a size of the light source,
a size of a circuit board, and
a size of an animal's nose.

12. The lighting device of claim 3, wherein the inner casing and the outer casing are cylindrical domes to produce uniformly diffused light.

13. A lighting device for acquiring nose pattern images, comprising:
an indirect illumination unit attached to a front of a camera lens in a camera device, including a smart phone;
a suction unit that affixes the indirect illumination unit in front of the camera lens; and
a pairing subunit that joins the indirect illumination unit and the suction unit.

* * * * *